United States Patent
Gozu et al.

(10) Patent No.: US 9,795,811 B2
(45) Date of Patent: Oct. 24, 2017

(54) EXPRESSION PROMOTING AGENT FOR CLOCK GENE AND HYALURONIC ACID SYNTHASE GENE

(75) Inventors: Yoko Gozu, Yokohama (JP); Shinichiro Haze, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 14/347,686

(22) PCT Filed: Sep. 29, 2011

(86) PCT No.: PCT/JP2011/005513
§ 371 (c)(1),
(2), (4) Date: May 28, 2014

(87) PCT Pub. No.: WO2013/046272
PCT Pub. Date: Apr. 4, 2013

(65) Prior Publication Data
US 2014/0255527 A1  Sep. 11, 2014

(51) Int. Cl.
| A61K 8/86 | (2006.01) |
| A61Q 19/00 | (2006.01) |
| A61K 8/97 | (2017.01) |
| A61K 36/53 | (2006.01) |
| A61K 36/61 | (2006.01) |
| A61K 8/33 | (2006.01) |

(52) U.S. Cl.
CPC .............. *A61Q 19/007* (2013.01); *A61K 8/33* (2013.01); *A61K 8/86* (2013.01); *A61K 8/97* (2013.01); *A61K 36/53* (2013.01); *A61K 36/61* (2013.01); *A61Q 19/00* (2013.01); *A61K 2800/5922* (2013.01)

(58) Field of Classification Search
None
See application file for complete search history.

(56) References Cited

U.S. PATENT DOCUMENTS

| 2003/0180335 | A1 | 9/2003 | Hamano |
| 2007/0026025 | A1* | 2/2007 | Mitchell ................ A61K 8/042 424/400 |
| 2007/0098669 | A1* | 5/2007 | Rosen .............................. 424/74 |
| 2009/0220481 | A1 | 9/2009 | Maes |
| 2010/0209370 | A1 | 8/2010 | Ohmori et al. |
| 2013/0022635 | A1 | 1/2013 | Gozu |
| 2013/0022692 | A1 | 1/2013 | Umishio |

FOREIGN PATENT DOCUMENTS

| JP | 10-182402 | 7/1998 |
| JP | 2000290163 | 10/2000 |
| JP | 2003-221333 | 8/2003 |
| JP | 2004-018411 | 1/2004 |
| JP | 2004-083541 | 3/2004 |
| JP | 2005139094 A2 | 6/2005 |
| JP | 2005220112 A2 | 8/2005 |
| JP | 2005225837 | 8/2005 |
| JP | 2006-241042 | 9/2006 |
| JP | 2008-266319 | 11/2008 |
| JP | 2009155227 | 7/2009 |
| JP | 2009-298765 | 12/2009 |
| JP | 2010-098965 | 5/2010 |
| WO | 2011122040 A1 | 10/2011 |
| WO | 2011122041 A1 | 10/2011 |

OTHER PUBLICATIONS

Miyahara et al., Development of Novel Multifunctional Cosmetic Raw Materials and Their Applications. IV. The Effect of Structure of Polyoxyethylene /Polyoxypropylene Derivative on the Self-organizing Structures of Surfactants, 2009, J Oleo Sci, 58:65-73.*
English Abstract of JP 2009-298765, 1 page.
English Abstract of JP 2008-266319, 2 pages.
English Abstract of JP 2010-098965, 1 page.
English Abstract of JP 2004-083541, 1 page.
English Abstract of JP 10-182402, 1 page.
English Abstract of JP 2003-221333, 1 page.
English Abstract of JP 2006-241042, 1 page.
English Abstract of JP 2004-018411, 1 page.
A.B. Reddy and J.S. O'Neill, "Healthy Clocks, Healthy Body, Healthy Mind", Trends in Cell Biol., vol. 20, No. 1, pp. 36-44, 2010, 9 pages.
M. Tanioka, et al. "Molecular Clocks in Mouse Skin", Journal of Investigative Dermatology, vol. 129, pp. 1225-1231, 2009, 7 pages.
R.V. Kondratov et al., "Early Aging and Age-Related Pathologies in Mice Deficient in BMAL1, the Core Component of the Circadian Clock", Genes & Development, vol. 20, pp. 1868-1873, 2006, 6 pages.
R. Tammi, et al., "Degradation of Newly Synthesized High Molecular Mass Hyaluronan in the Epidermal and Dermal Compartments of Human Skin in Organ Culture", Invest Dermatol., vol. 97, pp. 126-130, 1991, 5 pages.
K. Nagai, "Scents Controlling Appetite: Their Mechanisms", No. 246, pp. 31-44, 2010, 16 pages.
S. Watanabe and J. Imanishi, "Aromatherapy", Anti-Aging Igaku-Japanese Society of Anti-Aging Medicine Zasshi, vol. 5, No. 3, pp. 375-379, 2009, 5 pages.
International Search Report, International Application No. PCT/JP2011/005513, dated Dec. 20, 2011, 4 pages.
Extended European Search Report dated Jun. 12, 2015 issued in the corresponding European patent application No. 11873013.4.
Chinese Office Action dated Jul. 16, 2015 issued in the corresponding Chinese patent application No. 201180073869.3 and English translation thereof.
European Office Action dated May 6, 2016 issued in the corresponding European patent application No. 11873013.4.
Japanese Office Action dated May 6, 2016 issued in the corresponding Japanese patent application No. 2013-535637 and its English translation thereof.
Japanese Office Action dated Sep. 24, 2015 issued in the corresponding Japanese patent application No. 2013-535637, and English translation thereof.

(Continued)

*Primary Examiner* — Terry A McKelvey
*Assistant Examiner* — Catheryne Chen
(74) *Attorney, Agent, or Firm* — Rankin, Hill & Clark LLP (57) ABSTRACT

A method for promoting expression of a clock gene and/or a hyaluronic acid synthase gene in skin, comprising applying onto skin a composition comprising one kind or two kinds selected from lavender oil and eucalyptus oil, and an alkylene oxide derivative.

2 Claims, 4 Drawing Sheets

(56) References Cited

OTHER PUBLICATIONS

Japanese Office Action dated Mar. 28, 2017 issued in the corresponding Japanese patent application No. 2016-137431 and its English translation.
Japanese Office Action dated May 9, 2017 issued in the corresponding Japanese patent application No. 2016-137430 and its English translation.
Hiroyuki Yasui et al., Dermatological suppressive effect of lavender oil against UVA-induced reactive oxygen species ROS) in the skin of live animals: Possibility of lavender oil for both protection of ultraviolet light-induced dermal injury and suppression of skin-aging, Aroma Research, vol. 5, No. 2, pp. 129-135, 2004.; English abstract included; Cited in JPOA dated Mar. 28, 2017.
Arun K Mishra et at., Phytochemical Screening and Antioxidant Activity of essential oil of Eucalyptus leaf, Pharmacognosy Journal, vol. 2, No. 16, pp. 25-28, 2010.; Cited in JPOA dated Mar. 28, 2017.
Eucalyptus Essential Oil. Herbal. Lifestyle, 2010 [online], Oct. 8, 2010, [Mar. 15, 2017 search], the Internet <URL: http://www.herbal-essences.org/eucalyptus-essential-oil/>.; Cited in JPOA dated Mar. 28, 2017.
Haze Shinichiro, Application of the efficacy of aroma chemicals to cosmetic product development, Fragrance journal, vol. 33, No. 4, pp. 14-19, 2005.; English abstract included; Cited in JPOA dated Mar. 28, 2017.
Hiroyuki Yoshida et al., Effects of aromatic agents on hyaluronan synthesis in the skin, Fragrance journal, vol. 32, No. 8, pp. 36-40, 2004.; English abstract included; Cited in JPOA dated Mar. 28, 2017.

\* cited by examiner

A — EFFECT OF ALKYLENE OXIDE DERIVATIVE ON PROMOTION OF Bmal1 EXPRESSION BY EUCALYPTUS OIL B — EFFECT OF ALKYLENE OXIDE DERIVATIVE ON PROMOTION OF HAS2 EXPRESSION BY EUCALYPTUS OIL EUCALYPTUS OIL   □ 0ppm   ▨ 25ppm   ▨ 50ppm   ■ 100ppm

EXPRESSION PROMOTING AGENT FOR CLOCK GENE AND HYALURONIC ACID SYNTHASE GENE

TECHNICAL FIELD

The present invention relates to an agent for promoting expression of a clock gene and a hyaluronic acid synthase gene, and a method therefor.

BACKGROUND ART

Almost all living organisms on the earth internally have "biological clock" that autonomously oscillates with a cycle of approximately 24 hours. The biological clock is thought to cause biological circadian fluctuation referred to as a circadian rhythm to govern circadian fluctuation of various biological phenomena (activity), including a living organism sleep-wake cycle, body temperature, blood pressure, hormonal secretion, metabolism, and also mental and physical activity, and eating. Circadian rhythm disturbance has been recently pointed out as a factor of various mental and physical symptoms or disease onset, such as sleep disorder, a skin disease, a lifestyle-related disease, and also neuropsychiatric disorder including depression.

The biological clock is controlled by a rhythm-generating system including a gene cluster referred to as "clock gene." In the case of mammals, a feedback loop formed of promotion/suppression of transcription of a gene that codes four core proteins, CLOCK, BMAL, PERIOD and CRYPTOCHROME, is thought to form a core of a clock molecular mechanism, and if genes related to these core loops are not well expressed, to cause various diseases, including depression and a lifestyle-related disease (Non-Patent Literature 1).

A circadian rhythm control center (central clock) exists in a suprachiasmatic nucleus of hypothalamus. However, the clock gene has become clear to be expressed also in a peripheral tissue to form the circadian rhythm in a similar system. The clock gene is expressed also in skin, and in a manner similar to other organs, the clock gene beats out a rhythm in synchronization with a circadian rhythm center in a brain to maintain homeostasis (Non-Patent Literature 2).

For example, skin atrophy or suppression of body hair reproduction is seen in a BMAL1 knockdown animal, and if the clock gene does not satisfactorily work, skin health is adversely affected (Non-Patent Literature 3).

Hyaluronic acid is one kind of glycosaminoglycan, and widely exists in a living body, including a joint. Hyaluronic acid exists also in skin and is related to skin moistening and flexibility. Further, hyaluronic acid in skin is reported to be metabolized in a unit of approximately one day, and this quick metabolism is reported to contribute to keeping of good skin health by removal of a hazardous substance or the like (Non-Patent Literature 4).

For example, Patent Literature 1 describes that a strawberry seed extract promotes expression of a hyaluronic acid synthase gene or the like to have moistening action and skin-beautifying action.

CITATION LIST

Patent Literature

Patent literature 1: Japanese Unexamined Patent Publication No. 2009-298765

Non-Patent Literature

Non-Patent Literature 1: A. B. Reddy and J. S. O'Neill, "Healthy clocks, healthy body, healthy mind", Trends in Cell Biol., Vol. 20, No. 1, pp. 36-44, 2010

Non-Patent Literature 2: M. Tanioka et al., "Molecular Clocks in Mouse Skin", Journal of Investigative Dermatology, Vol. 129, pp. 1225-1231, 2009

Non-Patent Literature 3: R. V. Kondratov et al., "Early aging and age-related pathologies in mice deficient in BMAL1, the core component of the circadian clock", GENES & DEVELOPMENT, Vol. 20, pp. 1868-1873, 2006

Non-Patent Literature 4: R. Tammi et al., "Degradation of Newly Synthesized High Molecular Mass Hyaluronan in the Epidermal and Dermal Compartments of Human Skin in Organ Culture", Invest Dermatol., Vol. 97, pp. 126-130, 1991

SUMMARY OF INVENTION

Technical Problem

The present inventors have found that a specific plant extract can promote expression of a clock gene and a hyaluronic acid synthase gene. An object of the invention in the present application is to provide an agent for further effectively allowing enhancement of promotion of expression of a clock gene and a hyaluronic acid synthase gene by such a plant extract, and a method therefor.

Solution to Problem

The present inventors have found that lavender oil and eucalyptus oil promote expression of a clock gene such as Bmal and Period as related to a core loop of circadian rhythm control, and expression of a hyaluronic acid synthase gene, and that a plant extract thereof is compounded with an alkylene oxide derivative, thereby further effectively allowing promotion of expression of the genes, and thus have completed the present invention.

An expression promoting agent for the clock gene or an expression promoting agent for the hyaluronic acid synthase gene according to the present invention has features of comprising one kind or two kinds selected from lavender oil and eucalyptus oil, and an alkylene oxide derivative represented by general formula (I):

$$R^1O\text{-}[(AO)_m(EO)_n]\text{-}R^2 \qquad (I)$$

wherein, AO represents an oxyalkylene group having 3 to 4 carbon atoms; EO represents an oxyethylene group; m and n independently represent an average number of moles of the oxyalkylene group having 3 to 4 carbon atoms added and the oxyethylene group added, respectively, and satisfy expressions: $1 \le m \le 70$ and $1 \le n \le 70$, wherein a ratio of the oxyethylene group to a total of the oxyalkylene group and the oxyethylene group is 20 to 80% by mass. The oxyalkylene group and the oxyethylene group may be added in a block form or random form. $R^1$ and $R^2$ may be the same or different, and represent a hydrocarbon group having 1 to 4 carbon atoms or a hydrogen atom, wherein a ratio of number of hydrogen atoms to number of hydrocarbon groups in $R^1$ and $R^2$ is 0.15 or less.

Moreover, a method for promoting expression of the clock gene and/or the hyaluronic acid synthase gene in skin according to the present invention has features of applying onto skin a composition containing one kind or two kinds selected from lavender oil and eucalyptus oil, and the alkylene oxide derivative represented by general formula (I).

Lavender oil and eucalyptus oil can promote expression of both the clock gene such as Bmal and Period, and the hyaluronic acid synthase gene, and are further compounded with the specific alkylene oxide derivative, thereby significantly allowing enhancement of an effect on promoting gene expression.

Advantageous Effects of Invention

According to the present invention, lavender oil and/or eucalyptus oil that promotes expression of both a clock gene and a hyaluronic acid synthase gene is compounded with the specific alkylene oxide derivative described above, thereby remarkably allowing enhancement of expression of the clock gene and the hyaluronic acid synthase in skin, regulating a skin circadian rhythm to promote keeping of good homeostasis, and simultaneously increasing production of hyaluronic acid that plays an important role on a skin moistening and barrier function to improve a skin state, and also allowing keeping of a healthy skin state.

DESCRIPTION OF EMBODIMENTS

An expression promoting agent for a clock gene and an expression promoting agent for a hyaluronic acid synthase gene according to the present invention contain lavender oil and/or eucalyptus oil as an active ingredient. Both of the essential oil are commercially available, and are briefly described below.

Lavender oil is essential oil obtained by performing steam distillation of a flower obtained by picking lavender (*Lavandula officinalis*) being a dwarf shrub belonging to Lamiaceae.

Eucalyptus oil is essential oil obtained by performing steam distillation of leaves, sprigs or the like of eucalyptus (for example, *Eucalypus globulus*) being an evergreen tall tree belonging to Myrtaceae.

In the present invention, lavender oil and eucalyptus oil may be used alone or in combination of two kinds.

Further, the expression promoting agent for the clock gene, or the like according to the present invention contains a specific alkylene oxide derivative represented by general formula (I) as an essential ingredient.

In the alkylene oxide derivative used in the present invention, AO represents an oxyalkylene group having 3 to 4 carbon atoms, and specific examples include an oxypropylene group, an oxybutylene group, an oxyisobutylene group, an oxytrimethylene group and an oxytetramethylene group. AO is preferably an oxypropylene group or an oxybutylene group.

Then, m represents an average number of moles of an oxyalkylene group having 3 to 4 carbon atoms added, and satisfies an expression: $1 \leq m \leq 70$, and preferably, $2 \leq m \leq 20$. Then, n represents an average number of moles of an oxyethylene group added, and satisfies an expression: $1 \leq n \leq 70$, and preferably, $2 \leq n \leq 20$. When the number of moles of the oxyalkylene group having 3 to 4 carbon atoms or the oxyethylene group exceeds 70, a sticky feeling tends to come out.

Moreover, a ratio of the oxyethylene to a total of the oxyalkylene group having 3 to 4 carbon atoms and the oxyethylene group is 20 to 80% by mass. If the ratio of the oxyethylene group is less than 20% by mass, in the case of use as an external preparation for skin, the preparation tends to be poor in a moist feeling, and if the ratio exceeds 80% by mass, the preparation tends to be poor in a smooth feeling.

An order of adding ethylene oxide and alkylene oxide having 3 to 4 carbon atoms is not particularly specified. Moreover, the oxyethylene group and the oxyalkylene group having 3 to 4 carbon atoms may be added in a block form or random form, and the block form includes not only a two-stage block but also a three-stage or more-stage block. In addition, in comparison with a material added in the block form, use of a material added in the random form gives a product having a further excellent use feeling particularly when the product is used as the external preparation for skin, and therefore the material added in the random form is preferred.

$R^1$ and $R^2$ represent a hydrocarbon group having 1 to 4 carbon atoms or a hydrogen atom, and specific examples of the hydrocarbon groups include a methyl group, an ethyl group, an n-propyl group, an isopropyl group, an n-butyl group, a sec-butyl group and a tert-butyl group. $R^1$ and $R^2$ are preferably a methyl group or an ethyl group. When a hydrocarbon group having 5 or more carbon atoms is used, hydrophilicity decreases, and when such a product is used as the external preparation for skin, a moist feeling decreases. $R^1$ and $R^2$ may be the same or different.

As $R^1$ and $R^2$, a same kind thereof may be used for both, a hydrocarbon group having 1 to 4 carbon atoms and a hydrogen atom are mixed therein, or different kinds of hydrocarbon groups having 1 to 4 carbon atoms may be mixed therein. However, a ratio of existence of the hydrocarbon group and the hydrogen atom in the hydrocarbon group of $R^1$ and $R^2$ is preferably, in terms of a ratio (Y/X) of number (Y) of hydrogen atoms to number (X) of the hydrocarbon group, 0.15 or less, and further preferably, 0.06 or less. When the ratio of Y/X exceeds 0.15, a sticky feeling tends to come out.

The alkylene oxide derivative used in the present invention is not particularly limited, and specific examples include POE(14) POP(7) dimethyl ether, POE(10) POP(10) dimethyl ether, POE(7) POP(12) dimethyl ether, POE(25) POP(25) dimethyl ether, POE(27) POP(13) dimethyl ether, POE(55) POP(28) dimethyl ether, POE(36) POP(41) dimethyl ether, POE(14) POB(7) dimethyl ether, POE(10) POP (10) diethyl ether, POE(10) POP(10) dipropyl ether and POE(10) POP(10) dibutyl ether (in addition, POE, POP and POB as described above are abbreviations of polyoxyethylene, polyoxypropylene and polyoxybutylene, respectively).

The alkylene oxide derivative used in the present invention can be produced by a publicly known method. For example, the alkylene oxide derivative can be obtained by performing addition polymerization of ethylene oxide and an alkylene oxide having 3 to 4 carbon atoms to a compound having a hydroxyl group, and then allowing an ether reaction of alkyl halide in the presence of an alkali catalyst. Alternatively, a commercial item may also be used.

The expression promoting agent for the clock gene or the expression promoting agent for the hyaluronic acid synthase gene according to the present invention may contain any other ingredient in addition to the essential ingredient, unless advantageous effects of the invention are adversely affected. Moreover, the promoters may be used alone or in combination with a medical agent having action for regulating expression of other clock genes, a medical agent for promoting production of hyaluronic acid, or the like.

A ratio of compounding lavender oil or eucalyptus oil (essential oil) with the alkylene oxide derivative is not particularly limited in the invention in the present application, as long as the advantageous effects of the invention in the present application can be attained, but is preferably, in terms of a mass ratio of essential oil:alkylene oxide derivative, in the range of 0.001:1 to 10:1, and further preferably, in the range of 0.01:1 to 1:1. A higher effect on promoting expression of genes can be obtained at such a compounding ratio.

The expression promoting agent for the clock gene or the expression promoting agent for the hyaluronic acid synthase gene according to the present invention is preferably compounded into an external preparation for skin and used therefor, although no limitation is made thereto. A composition prepared by compounding lavender oil and/or eucalyptus oil that promotes expression of both the clock gene and the hyaluronic acid synthase gene, and the specific alkylene oxide derivative is applied onto skin, thereby allowing regulation of a skin circadian rhythm to promote keeping of homeostasis, and simultaneously increasing production of hyaluronic acid that plays an important role on a skin moistening and barrier function to allow keeping of a healthy skin state.

In the case of compounding the materials into the external preparation for skin, an amount of compounding lavender oil or eucalyptus oil being the active ingredient is not particularly limited, as long as the advantageous effects of the invention in the present application can be demonstrated, but is ordinarily in the range of 0.1 to 1,000 ppm, and further preferably, in the range of 10 to 500 ppm, based on the total mass of the external preparation for skin.

Moreover, in the case of compounding the materials into the external preparation for skin, an amount of compounding the alkylene oxide derivative thereinto is not particularly limited, as long as the advantageous effects of the invention in the present application can be demonstrated, but is preferably in the range of 0.001 to 60% by mass, and further preferably, in the range of 0.01 to 10% by mass, based on the total mass. If the amount is less than 0.001% by mass, no effect can be occasionally demonstrated, and if compounding is made exceeding 60% by mass, a sticky feeling may be occasionally caused.

In the case of compounding the materials into the external preparation for skin, according to a dosage form (for example, a liquid agent, a powder agent, a granule agent, an aerosol agent, a solid agent, a gel agent, a patch agent or a suppository), or a product form (for example, a cosmetic material, a pharmaceutical preparation and a quasi drug), the preparation may contain any ingredient ordinarily contained in such an external preparation for skin, together with the expression promoting agent for the clock gene or the expression promoting agent for the hyaluronic acid synthase gene according to the present invention. The external preparation for skin is described under a concept encompassing the composition in general to be applied onto skin (also including scalp, head hair and a nail), and specific examples include a cosmetic material such as a basic cosmetic material, a makeup cosmetic material, a hair cosmetic material, a skin or hair cleansing preparation, and various pharmaceutical preparations or quasi drugs, such as an ointment, a patch agent, a suppository and tooth paste. The dosage form is not particularly limited, either, and specific examples include any form such as an aqueous solution base, a solubilization base, an emulsion base, an oil base, a gel base, a paste base an ointment base, an aerosol base, a water-oil two-phase base and water-oil-powder three-phase base. When the external preparation for skin is a cosmetic material, specific examples include perfume, eau de toilette, eau de Cologne, cream, milky lotions, a skin lotion, foundations, face powder, a lip stick, soap, shampoos and rinses, a body shampoo, a body rinse, body powders and bathing agents.

In addition, examples of operating modes according to the present invention are described, but the present invention is not limited thereto, and the product can be used in any mode, as long as the advantageous effects of the invention can be attained. Moreover, in addition to the expression promoting agent for the gene according to the present invention, any other medical agent or the like can be compounded thereinto according to a specific mode, unless the advantageous effects of the invention are adversely affected.

A specific application of the expression promoting agent for the clock gene or the expression promoting agent for the hyaluronic acid synthase gene, or an object prepared by compounding the promoter according to the present invention is not particularly limited, if the application relates to circadian rhythm moderation and/or hyaluronic acid production. In particular, the promoters or the object is useful for the circadian rhythm moderation in skin and/or promotion of hyaluronic acid production therein, and can be applied to, for example, enhancement of skin moistening or flexibility, prevention or improvement of wrinkled skin, and prevention, improvement or therapy of various skin symptoms such as rough skin.

In the present invention, the clock gene is not limited, and specific examples include Bmal (Bmal1, Bmal2), Period (Period1, Period2, Period3), Clock, Cryptochrome, albumin site D-binding protein (Dbp), E4BP4, Npas2 and Rev-erb, above all, Bmal, Period, Clock and/or Cryptochrome being a biological clock core gene, and particularly, Bmal and/or Period.

EXAMPLES

The present invention is specifically described below by way of Examples, but the present invention is not limited to the Examples described below. As a culture cell used for evaluation, various cells can be used, such as a dermal fibroblast, an epithelial cell, an endothelial cell, a pigment cell, a fat cell and a nerve cell, but in the present Examples, evaluation was carried out using a human dermal fibroblast. A core system of a clock gene is common in all organism species and cell species, and therefore results of evaluation in the human dermal fibroblast are thought to be reflectable to other organism species and cell species.

Moreover, as the clock gene, an amount of expression of a Bmal gene (typified by Bmal1) or a Period gene (typified by Period1) in connection with the core system was measured. As a hyaluronic acid synthase gene, an amount of expression of hyaluronic acid synthase gene 2 (HAS2) was measured. Although no data were shown, when cortisol or forskolin was used as a medical agent for stimulation in a cultured human dermal fibroblast system, Bmal1 and HAS2 were confirmed to beat out a circadian rhythm having a peaked expression amount after approximately 16 hours from stimulation by the medical agent, and Period1 was confirmed to beat out such a circadian rhythm after 2 hours therefrom. In experiments described below, a gene expression amount after 16 hours or 2 hours from the stimulation was used as an index, respectively, and an effect on promotion of expression of the Bmal gene, the Period gene and the HAS2 gene being a test substance was evaluated.

Evaluation of Effect on Promotion of Expression of Clock Gene and Hyaluronic Acid Synthase Gene by Lavender Oil and Eucalyptus Oil As a cultured human dermal fibroblast, a commercially available normal human dermal fibroblast derived from adult skin (Cell Application, Inc) was purchased, and used for an experiment. Seeding was made in a DMEM culture medium prepared by adding 10% FBS, 20 mM HEPES, Glutamax and an antibacterial agent, and culture was made at 37° C. under 5% CO2. On the 6th day of culture, exchange was made to a testing culture medium containing lavender oil (0, 10, 25 or 50 ppm) or eucalyptus oil (0, 25, 50 or 100 ppm) at each concentration, time immediately after exchange was taken as 0 hours, and a sample of a cell was taken after 2 hours and 16 hours. From the cell taken therefrom, RNA was extracted using a commercially available RNA extraction kit, and an expression amount of a clock gene (Period1, Bmal1) and a hyaluronic acid synthase gene (HAS2) was measured using a commercially available PCR primer (Perfect Real Time Primer, TAKARA BIO INC.) according to an RT-PCR method. In a similar manner, an expression amount of RPLP0 being a housekeeping gene was quantified, and used as an internal standard to calculate a relative expression amount of an objective gene to an expression amount of RPLP0. A value obtained was subjected to a Dunnett's multiple comparison test, and a value having a significant difference in a 5% significance level on one side in comparison with a control (no essential oil addition) was judged to be effective.

Figure 1:
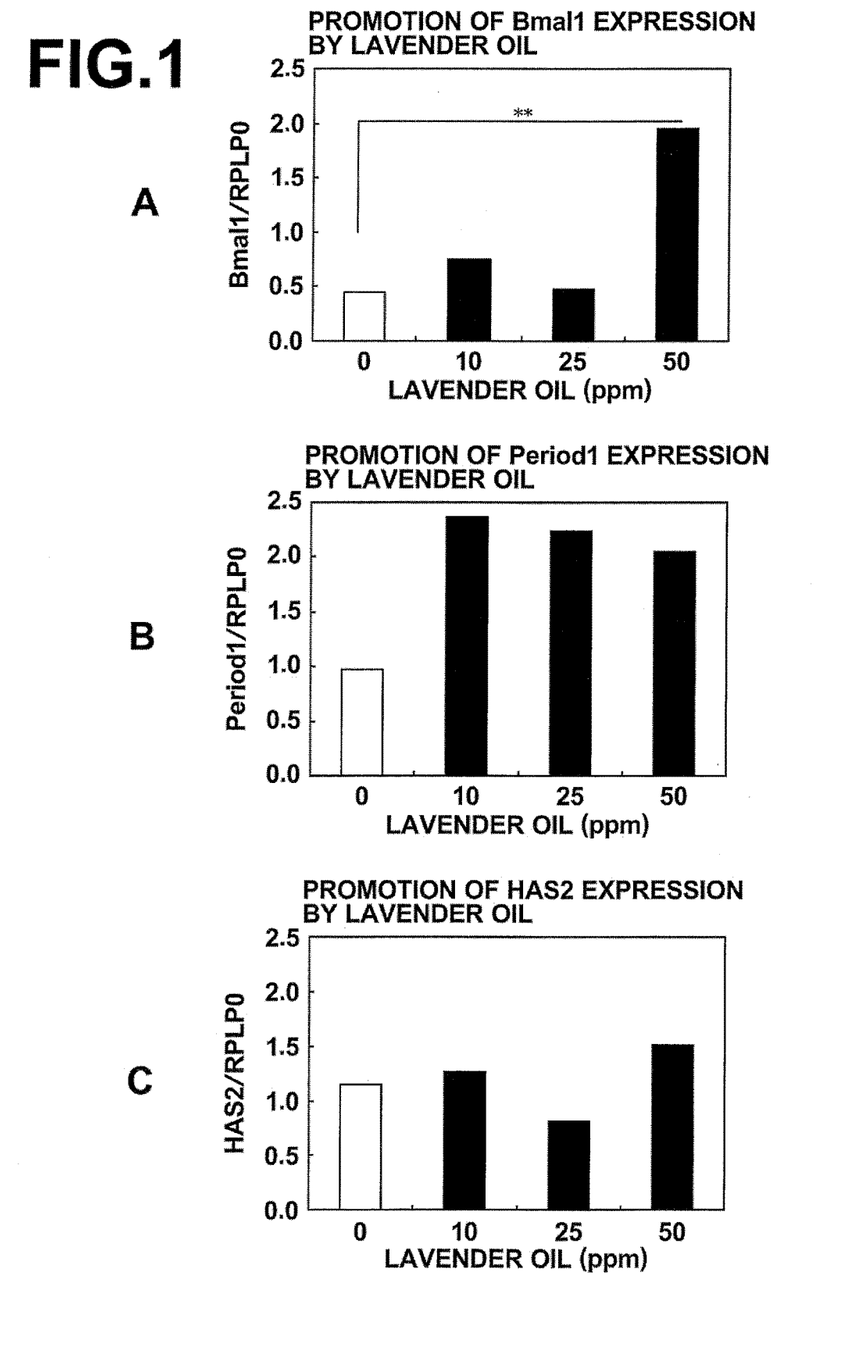
FIG. 1 is a graph showing promotion of expression of Bmal1 clock gene (A), Period1 clock gene (B) and HAS2 hyaluronic acid synthase gene (C) by lavender oil in a cultured human dermal fibroblast.
Figure 2:
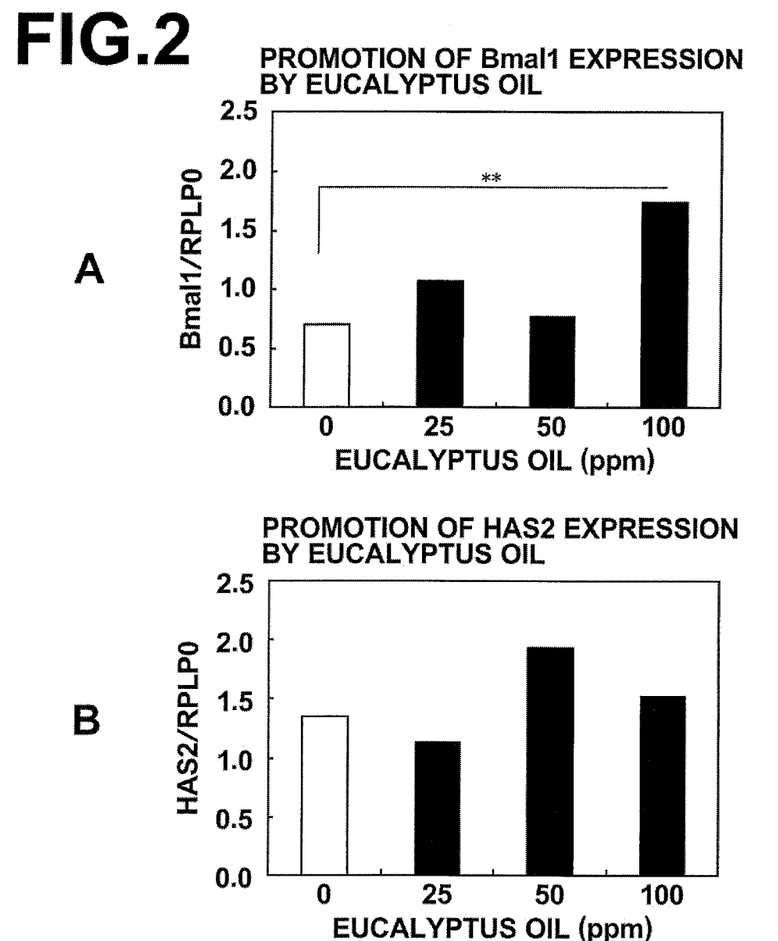
FIG. 2 is a graph showing promotion of expression of Bmal1 clock gene (A) and HAS2 hyaluronic acid synthase gene (B) by eucalyptus oil in a cultured human dermal fibroblast.

A through C of FIG. 1 show results using lavender oil, and A and B of FIG. 2 show results using eucalyptus oil. The results after 16 hours from stimulation were shown for Bmal1 and HAS2, and the results after 2 hours from stimulation were shown for Period1, respectively. In the Figures, the significant difference was shown by a symbol * ($P<0.05$) and a symbol ** ($P<0.01$).

FIG. 1 shows that lavender oil significantly enhances expression of all of Bmal1, Period1 and HAS2, and FIG. 2 shows that eucalyptus oil also enhances expression of Bmal1 and HAS2, and such essential oil is shown to allow promotion of expression of both a clock gene and a hyaluronic acid synthase gene.

Evaluation of Effect of Alkylene Oxide Derivative on Promotion of Expression of Clock Gene and Hyaluronic Acid Synthase Gene by Lavender Oil and Eucalyptus Oil An effect was evaluated on promotion of expression of a clock gene and a hyaluronic acid synthase gene by compounding an alkylene oxide derivative together with lavender oil or eucalyptus oil. In addition, as the alkylene oxide derivative, polyoxyethylene (14 mol) polyoxypropylene (7 mol) dimethyl ether (random polymer) was used.

In a similar manner as described above, a normal human dermal fibroblast derived from adult skin (Cell Application, Inc) was seeded, and on the 6th day of culture, exchange was made to a testing culture medium containing alkylene oxide derivative (0 to 0.1%) in a predetermined concentration, and lavender oil (0, 10, 25 or 50 ppm) or eucalyptus oil (0, 25, 50 or 100 ppm) in each concentration, time immediately after exchange was taken as 0 hours, and a sample of a cell was taken after 2 hours and 16 hours. In a similar manner described above, from the cell taken therefrom, RNA was extracted using a commercially available RNA extraction kit, and a gene expression amount of Bmal1, Period1, HAS2 and RPLP0 being a housekeeping gene was measured using a commercially available PCR primer (Perfect Real Time Primer, TAKARA BIO INC.) according to an RT-PCR method to calculate a relative expression amount of an objective gene to an expression amount of RPLP0. A value obtained was subjected to a Dunnett's multiple comparison test, and a value having a significant difference in a 5% significance level on one side in comparison with a control (no alkylene oxide derivative addition for essential oil in each concentration) was judged to be effective.

Figure 3:
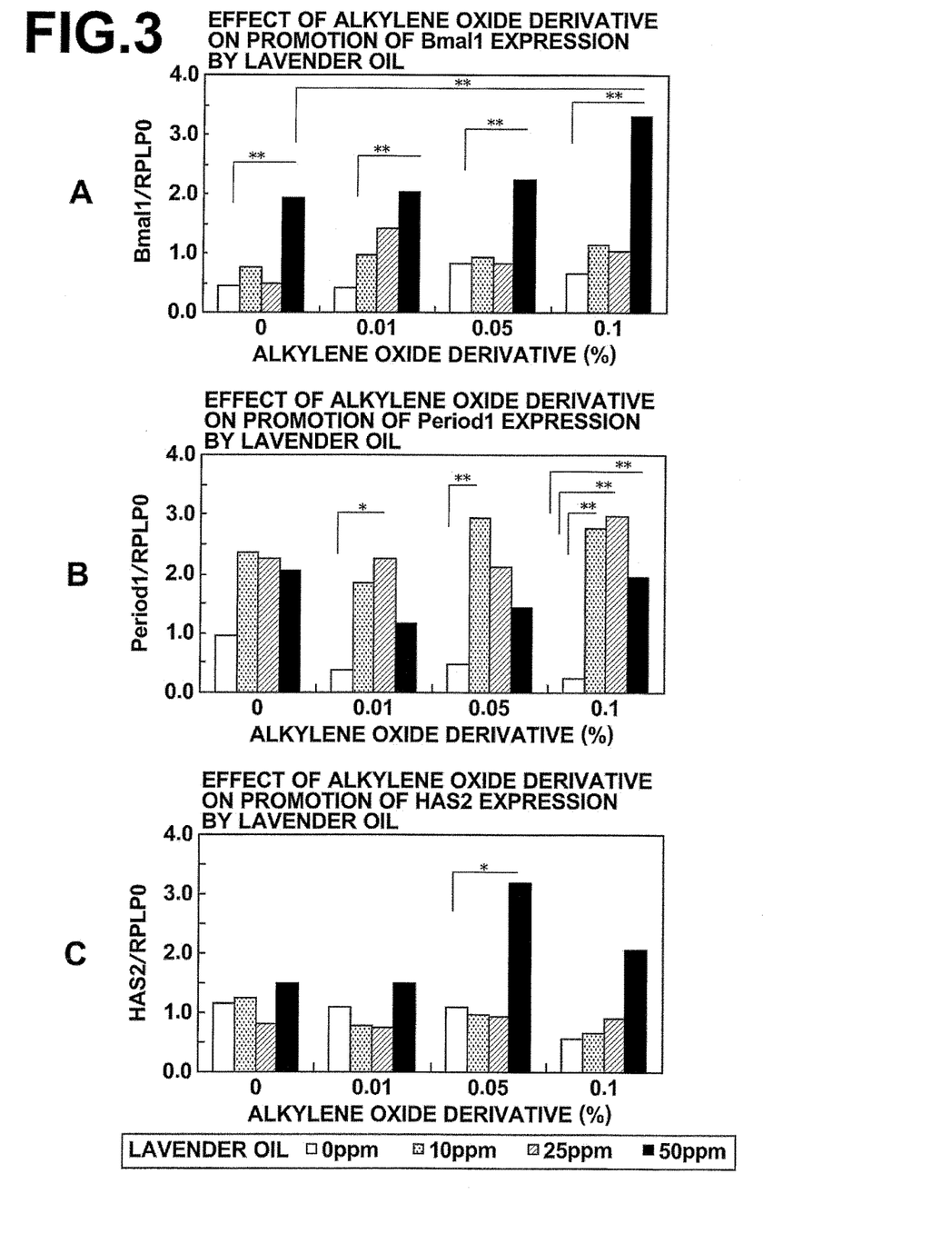
FIG. 3 is a graph showing an effect of an alkylene oxide derivative on promotion of expression of Bmal1 clock gene (A), Period1 clock gene (B) and HAS2 hyaluronic acid synthase gene (C) by lavender oil in a cultured human dermal fibroblast.
Figure 4:
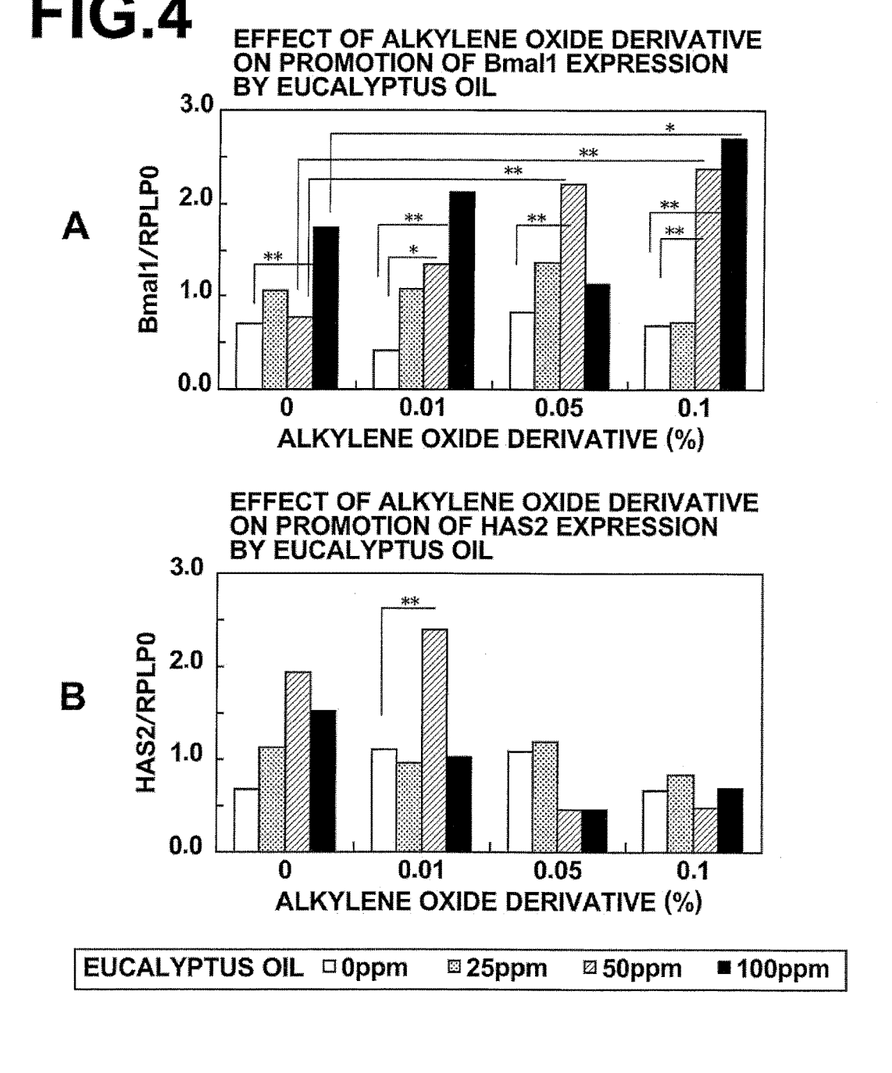
FIG. 4 is a graph showing an effect of an alkylene oxide derivative on promotion of expression of Bmal1 clock gene (A) and HAS2 hyaluronic acid synthase gene (B) by eucalyptus oil in a cultured human dermal fibroblast.

A through C of FIG. 3 show results using lavender oil, and A and B of FIG. 4 show results using eucalyptus oil. The results after 16 hours from stimulation were shown for Bmal1 and HAS2, and the results after 2 hours from stimulation were shown for Period1, respectively. In the Figures, the significant difference was shown by a symbol * ($P<0.05$) and a symbol ** ($P<0.01$).

A through C of FIG. 3 show that expression of Bmal1, Period1 and HAS2 is significantly enhanced by compounding the alkylene oxide derivative together with lavender oil in comparison with a case of lavender oil alone (alkylene oxide derivative: 0%). Moreover, A of FIG. 4 shows that expression of Bmal1 is significantly enhanced by compounding the alkylene oxide derivative together with eucalyptus oil in comparison with a case of eucalyptus oil alone (alkylene oxide derivative: 0%).

The results described above show that the alkylene oxide derivative is compounded together with lavender oil or eucalyptus oil, thereby further effectively allowing promotion of expression of the clock gene and the hyaluronic acid synthase gene to moderate the skin circadian rhythm, and simultaneously enhancing production of hyaluronic acid in skin to allow improvement or enhancement of a skin function.

Formulation Example

Formulation Examples are shown below for an expression promoting agent for a clock gene or an expression promoting agent for a hyaluronic acid synthase gene according to the present invention.

| Formulation Example 1 | Mass (%) |
|---|---|
| Eucalyptus oil | 0.1 |
| $CH_3O(EO)_{10}(PO)_{10}(EO)_{10}CH_3$ | 1.0 |

| Formulation Example 2 | Mass (%) |
|---|---|
| Lavender oil | 0.4 |
| $CH_3O(EO)_{14}(PO)_7CH_3$ | 1.0 |

| Formulation Example 3 | Mass (%) |
|---|---|
| Lavender oil | 1.0 |
| $CH_3O[(EO)_{20}/(PO)_{10}]CH_3$ | 20.0 |

| Formulation Example 4 | Mass (%) |
|---|---|
| Eucalyptus oil | 0.2 |
| Lavender oil | 0.5 |
| $CH_3O(EO)_{14}(PO)_7CH_3$ | 10.0 |

Compounding Example

Compounding Examples are shown below as application examples for an expression promoting agent for a clock gene or an expression promoting agent for a hyaluronic acid synthase gene according to the present invention. All compounding amounts are shown in terms of % by mass based on the total amount of a product.

| Skin Lotion | % by mass |
|---|---|
| (1) Glycerin | 2.0 |
| (2) Dipropylene glycol | 2.0 |
| (3) Polyethylene glycol-60 hydrogenated castor oil | 0.3 |
| (4) Xylitol | 3 |
| (5) Ascorbic acid | 0.005 |
| (6) Edetate trisodium | 0.1 |
| (7) Dye | 0.1 |
| (8) Expression promoting agent for a gene according to the present invention (Formulation Example 1) | 0.5 |
| (9) Purified water | Balance |

| Milky Lotion | % by mass |
|---|---|
| (1) Ethyl alcohol | 10.0 |
| (2) Glycerin | 3.0 |
| (3) Butylene glycol | 2.0 |
| (4) Polyethylene glycol | 3.0 |
| (5) Carboxyvinyl polymer | 0.1 |
| (6) Acrylic acid/alkyl acrylate copolymer | 0.1 |
| (7) Potassium hydroxide | 0.1 |
| (8) Cyclomethicone | 4.0 |
| (9) Squalane | 2.0 |
| (10) Spherical polyethylene | 2.0 |
| (11) Menthol | 0.5 |
| (12) Medical agent | 0.1 |
| (13) Paraben | 0.1 |
| (14) Edetate trisodium | 0.1 |
| (15) Pigment | 0.1 |
| (16) Expression promoting agent for a gene according to the present invention (Formulation Example 2) | 1.0 |
| (17) Purified water | Balance |

| Cream | % by mass |
|---|---|
| (1) Glycerin | 10.0 |
| (2) Butylene glycol | 5.0 |
| (3) Carbomer | 0.1 |
| (4) Potassium hydroxide | 0.2 |
| (5) Stearic acid | 2.0 |
| (6) Glyceryl stearate | 2.0 |
| (7) Glyceryl isostearate | 2.0 |
| (8) Vaseline | 5.0 |
| (9) Preservative | 0.1 |
| (10) Antioxidant | 0.1 |
| (11) Expression promoting agent for a gene according to the present invention (Formulation Example 3) | 1.0 |
| (12) Chelating agent | 1.0 |
| (13) Pigment | 0.01 |
| (14) Stearyl alcohol | 2.0 |
| (15) Behenyl alcohol | 2.0 |
| (16) Orange oil | 0.01 |
| (17) Hydrogenated palm kernel oil | 2.0 |
| (18) Squalane | 10.0 |
| (19) 4-Methoxysalicylic acid potassium salt | 3.0 |
| (20) Purified water | Balance |

| Cream | % by mass |
|---|---|
| (1) Glycerin | 3.0 |
| (2) Dipropylene glycol | 7.0 |
| (3) Polyethylene glycol | 3.0 |
| (4) Glyceryl stearate | 3.0 |
| (5) Glyceryl isostearate | 2.0 |
| (6) Stearyl alcohol | 2.0 |
| (7) Behenyl alcohol | 2.0 |
| (8) Liquid paraffin | 7.0 |
| (9) Cyclomethicone | 3.0 |
| (10) Dimethicone | 1.0 |
| (11) Octyl methoxycinnamate | 0.1 |
| (12) Sodium hyaluronate | 0.05 |
| (13) Preservative | 0.1 |
| (14) Antioxidant | 0.1 |
| (15) Expression promoting agent for a gene according to the present invention (Formulation Example 4) | 0.4 |
| (16) Chelating agent | 1.0 |
| (17) Pigment | 0.01 |
| (18) Purified water | Balance |

| Gel | % by mass |
|---|---|
| (1) Ethyl alcohol | 10.0 |
| (2) Glycerin | 5.0 |
| (3) Butylene glycol | 5.0 |
| (4) Carbomer | 0.5 |
| (5) Aminomethyl propanol | 0.3 |
| (6) Polyethylene glycol-60 hydrogenated castor oil | 0.3 |
| (7) Menthol | 0.02 |
| (8) Orange oil | 0.05 |
| (9) Preservative | 0.05 |
| (10) Chelating agent | 1.0 |
| (11) Expression promoting agent for a gene according to the present invention (Formulation Example 2) | 1.0 |
| (12) Purified water | Balance |

| Gel for Massage | % by mass |
|---|---|
| (1) Erythritol | 2.0 |
| (2) Caffeine | 5.0 |
| (3) Phellodendron amurense bark extract | 3.0 |
| (4) Glycerin | 50.0 |
| (5) Carboxyvinyl polymer | 0.4 |
| (6) Polyethylene glycol 400 | 30.0 |
| (7) Edetate trisodium | 0.1 |
| (8) Polyoxylene(10) methyopolysiloxane copolymer | 2.0 |

-continued

| Gel for Massage | % by mass |
|---|---|
| (9) Squalane | 1.0 |
| (10) Potassium hydroxide | 0.15 |
| (11) Expression promoting agent for a gene according to the present invention (Formulation Example 1) | 1.0 |
| (12) Purified water | Balance |

| Massage Cream | % by mass |
|---|---|
| (1) Solid paraffin | 5.0 |
| (2) Beeswax | 10.0 |
| (3) Vaseline | 15.0 |
| (4) Liquid paraffin | 41.0 |
| (5) 1.3-butylene glycol | 4.0 |
| (6) Glyceryl monostearate | 2.0 |
| (7) POE (20) sorbitan monolaurate | 2.0 |
| (8) Borax | 0.2 |
| (9) Caffeine | 2.0 |
| (10) Preservative | As needed |
| (11) Antioxidant | As needed |
| (12) Expression promoting agent for a gene according to the present invention (Formulation Example 2) | 1.0 |
| (13) Purified water | Balance |

The products according to Compounding Examples are applied onto skin by a typical operating mode of each product form to allow promotion of expression of the clock gene and the hyaluronic acid synthase gene to moderate the skin circadian rhythm, and enhancing production of hyaluronic acid production in skin to allow improvement in the skin state, and keeping of a healthy skin state.

The invention claimed is:

1. A method for promoting expression of hyaluronic acid synthase gene in skin, the method comprising applying onto skin a composition comprising lavender oil, and an alkylene oxide derivative represented by general formula (I):

$$R^1O\text{-}[(AO)_m(EO)_n]\text{-}R^2 \qquad (I)$$

wherein, AO represents an oxyalkylene group having 3 to 4 carbon atoms;

wherein EO represents an oxyethylene group;

wherein m and n independently represent an average number of moles of the oxyalkylene group having 3 to 4 carbon atoms added and the oxyethylene group added, respectively, and satisfy the expressions: $1 \leq m \leq 70$ and $1 \leq n \leq 70$;

wherein a ratio of the oxyethylene group to a total of the oxyalkylene group and the oxyethylene group is 20% to 80% by mass;

wherein the oxyalkylene group and the oxyethylene group may be added in a block form or random form;

wherein $R^1$ and $R^2$ may be the same or different, and represent a hydrocarbon group having 1 to 4 carbon atoms or a hydrogen atom;

wherein a ratio of number of hydrogen atoms to number of hydrocarbon groups of $R^1$ and $R^2$ is 0.15 or less;

wherein the amount of lavender oil is 50 ppm in the composition; and wherein the amount of the alkylene oxide derivative present in the composition is in the range of 0.05% to 0.1% by mass, based on the total mass of the composition.

2. The method according to claim 1, wherein:

the amount of the alkylene oxide derivative is 0.05% by mass, based on the total mass of the composition.

* * * * *